(12) United States Patent
Mittelstadt et al.

(10) Patent No.: US 9,950,202 B2
(45) Date of Patent: Apr. 24, 2018

(54) RESPIRATOR NEGATIVE PRESSURE FIT CHECK DEVICES AND METHODS

(71) Applicant: 3M INNOVATIVE PROPERTIES COMPANY, St. Paul, MN (US)

(72) Inventors: William A. Mittelstadt, Woodbury, MN (US); Carl W. Raines, III, Woodbury, MN (US); David R. Stein, White Bear Lake, MN (US); Nathan A. Abel, Minneapolis, MN (US); David M. Blomberg, Lino Lakes, MN (US); Michael J. Cowell, Woodbury, MN (US); Gary E. Dwyer, Mallorytown (CA); Thomas I. Insley, Lake Elmo, MN (US); Michael J. Svendsen, Blaine, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 568 days.

(21) Appl. No.: 13/757,373

(22) Filed: Feb. 1, 2013

(65) Prior Publication Data
US 2014/0216474 A1     Aug. 7, 2014

(51) Int. Cl.
*A61M 16/06*     (2006.01)
*A61M 16/20*     (2006.01)
(Continued)

(52) U.S. Cl.
CPC .......... *A62B 27/00* (2013.01); *A61M 16/0605* (2014.02); *A61M 16/20* (2013.01);
(Continued)

(58) Field of Classification Search
CPC .. A61M 16/00; A61M 16/06; A61M 16/0605; A61M 16/20; A61M 16/208;
(Continued)

(56) References Cited

U.S. PATENT DOCUMENTS

| 3,167,070 A | 1/1965 | Silverman |
| 3,879,586 A | 4/1975 | DuRocher et al. |

(Continued)

FOREIGN PATENT DOCUMENTS

| DE | 2645008 | 3/1979 |
| GB | 591531 | 8/1947 |

(Continued)

OTHER PUBLICATIONS

International Application PCT/US2014/012190 Search Report dated Sep. 12, 2014.
(Continued)

*Primary Examiner* — Keri J Nelson

(57) ABSTRACT

A respiratory mask body defining a breathable air zone for a wearer and having a shut-off valve is provided. In an exemplary embodiment, the mask body includes one or more inlet ports configured to receive one or more breathing air source components. The shut-off valve is operable between a closed position and an open position, and when in a closed position the shut-off valve prevents fluid communication between the one or more inlet ports and the breathable air zone and the shut-off valve returns to an open position in the absence of an applied force.

34 Claims, 6 Drawing Sheets

(51) Int. Cl.
- *A62B 9/02* (2006.01)
- *A62B 18/00* (2006.01)
- *A62B 18/10* (2006.01)
- *A62B 27/00* (2006.01)

(52) U.S. Cl.
CPC ............... *A62B 9/02* (2013.01); *A62B 18/10* (2013.01); *A62B 18/00* (2013.01)

(58) Field of Classification Search
CPC .......... A61M 16/209; F16K 3/00; F16K 3/02; F16K 3/04; F16K 3/06; F16K 3/08; A62B 18/00; A62B 18/006; A62B 18/025; A62B 18/10; A62B 19/00; A62B 31/00; A62B 7/00; A62B 7/02; A62B 7/04; A62B 9/00; A62B 9/02
USPC .......... 128/846, 848, 857, 859, 863, 200.24, 128/201.24, 201.28, 204.15, 205.24, 128/205.25, 206.21, 206.24, 207.12; 251/14–16, 57, 73, 149.8, 208
See application file for complete search history.

(56) References Cited

U.S. PATENT DOCUMENTS

| | | |
|---|---|---|
| 4,390,765 A | 6/1983 | Sado et al. |
| 4,414,973 A | 11/1983 | Matheson |
| 4,574,799 A | 3/1986 | Warncke |
| 4,604,509 A | 8/1986 | Clancy et al. |
| 4,790,306 A | 12/1988 | Braun |
| 4,905,683 A | 3/1990 | Cronjaeger |
| 4,981,134 A | 1/1991 | Courtney |
| 5,154,168 A * | 10/1992 | Schlobohm ............... 128/205.27 |
| 5,299,448 A | 4/1994 | Maryyanek |
| 5,372,130 A | 12/1994 | Stern |
| 5,501,213 A | 3/1996 | Jackson |
| 5,540,218 A | 7/1996 | Jones |
| 5,579,761 A | 12/1996 | Yuschak |
| 5,592,935 A | 1/1997 | Elstran |
| 5,647,356 A * | 7/1997 | Osendorf et al. ........ 128/206.17 |
| 5,647,357 A | 7/1997 | Barnett |
| 5,659,296 A | 8/1997 | Doebe |
| 5,669,375 A | 9/1997 | Dahrendorf |
| 5,687,767 A | 11/1997 | Bowers |
| 5,732,695 A | 3/1998 | Metzger |
| 5,803,076 A | 9/1998 | Myers |
| 5,937,857 A | 8/1999 | Caterini |
| 5,967,142 A | 10/1999 | Dorcheh |
| 6,016,802 A | 1/2000 | Jackson |
| 6,016,804 A | 1/2000 | Gleason |
| 6,167,882 B1 | 1/2001 | Almqvist |
| 6,196,223 B1 | 3/2001 | Belfer |
| 6,206,003 B1 * | 3/2001 | Burch ...................... 128/206.21 |
| 6,298,849 B1 | 10/2001 | Scholey |
| 6,345,620 B2 | 2/2002 | Salapow |
| 6,408,845 B1 | 6/2002 | Pereira |
| 6,418,928 B1 | 7/2002 | Bordewick |
| 6,460,539 B1 | 10/2002 | Japuntich |
| 6,575,165 B1 | 6/2003 | Cook |
| 6,584,976 B2 | 7/2003 | Japuntich |
| 6,659,102 B1 | 12/2003 | Sico |
| 6,712,072 B1 | 3/2004 | Lang |
| 6,761,169 B2 | 7/2004 | Eswarappa |
| 6,817,362 B2 | 11/2004 | Gélinas |
| 6,854,464 B2 | 2/2005 | Mukaiyama |
| 6,874,499 B2 | 4/2005 | Viner |
| 6,883,518 B2 | 4/2005 | Mittelstadt |
| 6,886,559 B2 | 5/2005 | McDonald |
| 6,997,206 B1 | 2/2006 | Klockseth |
| 7,025,060 B1 | 4/2006 | Nicholson |
| 7,059,326 B2 | 6/2006 | Heidmann |
| 7,100,608 B2 | 9/2006 | Brewer |
| 7,114,496 B1 | 10/2006 | Resnick |
| 7,118,608 B2 | 10/2006 | Lovell |
| 7,121,279 B2 | 10/2006 | Dennis |
| RE39,493 E | 2/2007 | Yuschak |
| 7,171,966 B2 | 2/2007 | Schrader |
| 7,188,622 B2 | 3/2007 | Martin |
| 7,213,595 B2 | 5/2007 | Capon |
| 7,296,568 B2 | 11/2007 | Capon |
| 7,302,951 B2 | 12/2007 | Mittelstadt |
| 7,320,722 B2 | 1/2008 | Mittelstadt |
| 7,353,826 B2 | 4/2008 | Sleeper |
| 7,464,705 B2 | 12/2008 | Tanizawa |
| 7,543,584 B2 | 6/2009 | Brookman |
| 7,584,751 B1 | 9/2009 | Brooks, Jr. |
| 7,587,929 B2 | 9/2009 | Zielinski |
| 7,650,884 B2 | 1/2010 | Flannigan |
| 7,669,599 B2 | 3/2010 | Gunaratnam |
| 7,762,258 B2 | 7/2010 | Zollinger |
| 7,827,990 B1 | 11/2010 | Melidis |
| 7,836,886 B2 | 11/2010 | McDonald |
| 7,849,856 B2 | 12/2010 | Mittelstadt |
| 7,866,319 B2 | 1/2011 | Penton |
| 7,997,275 B2 | 8/2011 | Quinn |
| 8,006,691 B2 | 8/2011 | Kenyon |
| 8,011,368 B2 | 9/2011 | Crutchfield |
| 8,066,006 B2 | 11/2011 | Daugaard |
| 8,069,853 B2 | 12/2011 | Tilley |
| 8,104,472 B2 | 1/2012 | Henderson |
| 8,118,026 B2 | 2/2012 | Gebrewold |
| 8,176,918 B2 | 5/2012 | Teng |
| 8,267,088 B2 | 9/2012 | Steindorf |
| 8,272,382 B2 | 9/2012 | Howard |
| 8,312,876 B2 | 11/2012 | Mutze |
| 8,327,850 B2 | 12/2012 | Ng |
| 8,336,547 B1 | 12/2012 | Ritchie |
| 8,342,180 B2 | 1/2013 | Martin |
| 8,365,771 B2 | 2/2013 | Xue |
| 8,402,966 B2 | 3/2013 | Morgan, III |
| 8,402,971 B2 | 3/2013 | Scheiner |
| 8,443,806 B2 | 5/2013 | Morelli |
| 8,460,423 B2 | 6/2013 | Legare |
| 8,496,005 B2 | 7/2013 | McDonald |
| 8,505,536 B2 | 8/2013 | Kielow |
| 8,528,559 B2 | 9/2013 | Crutchfield |
| 8,550,084 B2 | 10/2013 | Ng |
| 8,573,201 B2 | 11/2013 | Rummery |
| 8,631,792 B2 | 1/2014 | Ho |
| 8,678,003 B2 | 3/2014 | Darkin |
| 8,708,708 B1 | 4/2014 | Carideo |
| 8,720,443 B2 | 5/2014 | Kooij |
| 8,770,195 B2 | 7/2014 | Stone |
| 2005/0085799 A1 | 4/2005 | Luria |
| 2006/0225738 A1 | 10/2006 | Afentoulopoulos |
| 2006/0283453 A1 | 12/2006 | Haddad |
| 2006/0283455 A1 | 12/2006 | Walker |
| 2007/0272169 A1 | 11/2007 | Barney |
| 2008/0135050 A1 | 6/2008 | Hitchcock |
| 2008/0178884 A1 | 7/2008 | Gerson |
| 2009/0044808 A1 | 2/2009 | Guney |
| 2009/0065729 A1 | 3/2009 | Worboys |
| 2009/0078264 A1 | 3/2009 | Martin |
| 2009/0107515 A1 | 4/2009 | Gavriely |
| 2009/0139526 A1 | 6/2009 | Melidis |
| 2009/0188506 A1 | 7/2009 | Duke |
| 2009/0217926 A1 | 9/2009 | Hine |
| 2009/0235934 A1 | 9/2009 | Martin |
| 2009/0266361 A1 | 10/2009 | Bilger |
| 2010/0108067 A1 | 5/2010 | Walker |
| 2010/0132714 A1 * | 6/2010 | Morelli et al. ........... 128/206.21 |
| 2010/0206311 A1 | 8/2010 | Flannigan |
| 2010/0218761 A1 | 9/2010 | Flannigan |
| 2010/0224194 A1 | 9/2010 | Walker |
| 2010/0269833 A1 | 10/2010 | Gillotin |
| 2010/0307506 A1 | 12/2010 | Kielow |
| 2010/0313891 A1 | 12/2010 | Veliss |
| 2011/0000481 A1 | 1/2011 | Gumaste |
| 2011/0100372 A1 | 5/2011 | Betz |
| 2011/0240027 A1 | 10/2011 | Billingsley |
| 2011/0290253 A1 | 12/2011 | McAuley |
| 2012/0042878 A1 | 2/2012 | Woo |
| 2012/0080035 A1 | 4/2012 | Guney |

(56) References Cited

U.S. PATENT DOCUMENTS

| | | |
|---|---|---|
| 2012/0167890 A1 | 7/2012 | Insley |
| 2012/0168658 A1 | 7/2012 | Insley |
| 2012/0199130 A1 | 8/2012 | Euvrard |
| 2012/0204879 A1 | 8/2012 | Cariola |
| 2012/0234326 A1 | 9/2012 | Mazzone |
| 2012/0260920 A1 | 10/2012 | Choi |
| 2013/0004358 A1 | 1/2013 | Underwood, Jr. |
| 2013/0104900 A1 | 5/2013 | Tobias |
| 2013/0125896 A1 | 5/2013 | Dwyer |
| 2013/0133628 A1 | 5/2013 | Fornara |
| 2013/0133664 A1 | 5/2013 | Startare |
| 2013/0180523 A1 | 7/2013 | Huggins |
| 2013/0186394 A1 | 7/2013 | Hallett |
| 2013/0199520 A1 | 8/2013 | Dhuper |
| 2013/0228184 A1 | 9/2013 | Lee |
| 2013/0239972 A1 | 9/2013 | McAuley |
| 2013/0269513 A1 | 10/2013 | Estirado Vera |
| 2013/0298775 A1 | 11/2013 | Fiet |
| 2013/0319420 A1 | 12/2013 | Danford |
| 2013/0327323 A1 | 12/2013 | Rubin |
| 2014/0007888 A1 | 1/2014 | Sanchez Talero |
| 2014/0076325 A1 | 3/2014 | Rosert |
| 2014/0096768 A1 | 4/2014 | Lee |
| 2014/0096774 A1 | 4/2014 | Olsen |
| 2014/0190476 A1 | 7/2014 | Stinton |
| 2014/0216447 A1 | 8/2014 | Kihlberg |
| 2014/0216473 A1 | 8/2014 | Dwyer |
| 2014/0216474 A1 | 8/2014 | Mittelstadt |
| 2014/0216475 A1 | 8/2014 | Blomberg |
| 2015/0107596 A1 | 4/2015 | Mashiko |

FOREIGN PATENT DOCUMENTS

| | | |
|---|---|---|
| GB | 2 388 787 | 11/2003 |
| JP | 60-99946 | 7/1985 |
| JP | 60-99947 | 7/1985 |
| JP | 4-18584 | 4/1992 |
| JP | 3726260 | 6/2001 |
| WO | WO 2003/099385 | 12/2003 |
| WO | WO 2012/100116 | 7/2012 |
| WO | WO 2013/187278 | 12/2013 |
| WO | WO 2013/187279 | 12/2013 |

OTHER PUBLICATIONS

Koken Website, *Particulate Respirators*, web literature, http://www.koken-ltd.co.jp/english/particulaterespirators.htm., pp. 1-4, obtained from internet Jun. 3, 2013.

U.S. Appl. No. 14/285,202 to Mittelstadt et al. filed May 22, 2014, entitled Respirator Negative Pressure Fit Check Devices and Methods.

\* cited by examiner

RESPIRATOR NEGATIVE PRESSURE FIT CHECK DEVICES AND METHODS

TECHNICAL FIELD

This disclosure relates to respiratory protection devices and methods, in particular a respiratory protection device including a shut-off valve, and a method of performing a negative pressure fit check of a respirator protection device including a shut-off valve.

BACKGROUND

Respiratory protection devices commonly include a mask body and one or more filter cartridges that are attached to the mask body. The mask body is worn on a person's face, over the nose and mouth, and may include portions that cover the head, neck, or other body parts, in some cases. Clean air is made available to a wearer after passing through filter media disposed in the filter cartridge. In negative pressure respiratory protection devices, air is drawn through a filter cartridge by a negative pressure generated by a wearer during inhalation. Air from the external environment passes through the filter medium and enters an interior space of the mask body where it may be inhaled by the wearer.

In order to effectively deliver breathable air to a wearer, respiratory protection devices desirably provide an adequate seal to prevent unfiltered air from entering the mask. Various techniques have been proposed for testing the integrity of a seal provided by a respiratory protection device. In a positive pressure test, an exhalation valve of the respiratory protection device is blocked while the wearer exhales into the mask. An adequate seal may be signaled by an increased internal pressure due to the inability of air within the mask to escape through an exhalation valve if a leak is not present. Alternatively, negative pressure tests have been proposed in which a filter cartridge port is blocked while a wearer inhales while wearing the mask. An adequate seal may be signaled by a reduced internal pressure due to the inability of air to enter the mask if a leak is not present.

SUMMARY

The present disclosure provides a respiratory mask including a mask body defining a breathable air zone for a wearer and having one or more inlet ports configured to receive one or more breathing air source components, and a shut-off valve operable between a closed position and an open position. In a closed position the shut-off valve prevents fluid communication between the one or more inlet ports and the breathable air zone, and the shut-off valve returns to an open position in the absence of an applied force. In an exemplary embodiment, the mask body includes two or more inlet ports configured to receive two or more breathing air source components, and in a closed position the shut-off valve prevents fluid communication between the two or more clean air sources and the breathable air zone.

The present disclosure further provides a respiratory mask including a mask body defining a breathable air zone for a wearer and having one or more inlet ports configured to receive one or more breathing air source components, and a shut-off valve operable between a closed position and an open position. In a closed position the shut-off valve prevents fluid communication between the one or more inlet ports and the breathable air zone, and when the mask body is positioned for use on a wearer and a negative pressure is achieved after closing the shut-off valve and inhaling, the shut-off valve remains in the closed position due to a negative pressure in the breathable air zone.

The present disclosure further provides a respiratory mask including a mask body defining a breathable air zone for a wearer and having two or more inlet ports configured to receive two or more breathing air source components, and a shut-off valve operable between a closed position and an open position. In a closed position the shut-off valve prevents fluid communication between the two or more inlet ports and the breathable air zone, and inhalation by a wearer while the shut-off valve is in a closed position provides an indication of the presence of leaks around a periphery of the mask body.

The above summary is not intended to describe each disclosed embodiment or every implementation. The Figures and the Detailed Description, which follow, more particularly exemplify illustrative embodiments.

BRIEF DESCRIPTION OF DRAWINGS

The disclosure may be further explained with reference to the appended Figures, wherein like structure is referred to by like numerals throughout the several views, and wherein.

Figure 1A:
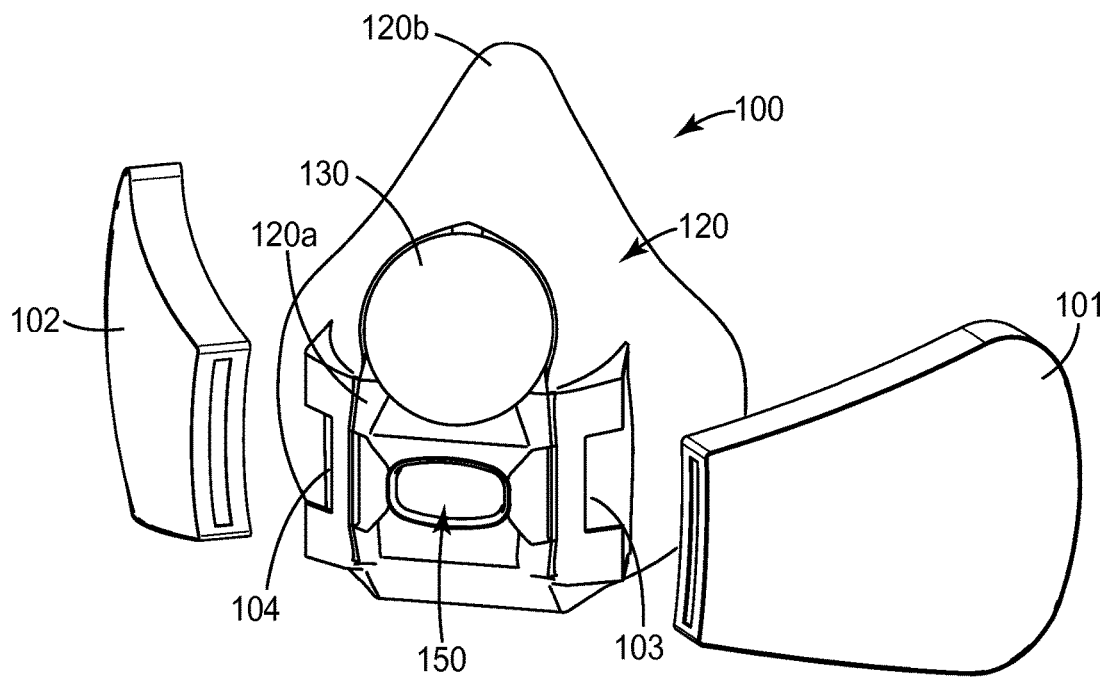
FIG. 1a is a front perspective view of an exemplary respiratory protection device according to the present disclosure.

While the above-identified figures set forth various embodiments of the disclosed subject matter, other embodiments are also contemplated. In all cases, this disclosure presents the disclosed subject matter by way of representation and not limitation. It should be understood that numerous other modifications and embodiments can be devised by those skilled in the art which fall within the scope and spirit of the principles of this disclosure.

DETAILED DESCRIPTION

The present disclosure provides a respiratory protection device including a mask body defining a breathable air zone for a wearer and having one or more inlet ports configured to receive one or more breathing air source components. A shut-off valve operable between a closed position and an open position is provided to allow a wearer to easily perform a negative pressure fit test. In a closed position, the shut-off valve prevents fluid communication between each of the one or more inlet ports and the breathable air zone. Inhalation by a wearer results in a negative internal pressure within the mask if the respiratory protection device is appropriately fitted and an adequate seal is achieved.

FIGS. 1a through 1d illustrate an exemplary respiratory protection device 100 that may cover the nose and mouth and provide breathable air to a wearer. The respiratory protection device 100 includes a mask body 120 including one or more inlet ports, such as a first inlet port 103, and/or a second inlet port 104. One or more breathing air source components may be positioned at the one or more inlet ports of mask body 120. In an exemplary embodiment, first and second breathing air source components 101, 102 are provided and include filter cartridges configured to be attached at first and second inlet ports 103 and 104. Filter cartridges 101, 102 filter air received from the external environment before the air passes into interior space within the mask body for delivery to a wearer.

The mask body 120 may include a rigid or semi-rigid portion 120a and a compliant face contacting portion 120b. The compliant face contacting portion of the mask body is compliantly fashioned for allowing the mask body to be comfortably supported over a person's nose and mouth and/or for providing an adequate seal with the face of a wearer to limit undesirable ingress of air into an interior of mask body 120, for example. The face contacting member 120b may have an inturned cuff so that the mask can fit comfortably and snugly over the wearer's nose and against the wearer's cheeks. The rigid or semi-rigid portion 120a provides structural integrity to mask body 120 so that it can properly support breathing air source components, such as filter cartridges 101, 102, for example. In various exemplary embodiments, mask body portions 120a and 120b may be provided integrally or as separately formed portions that are subsequently joined together in permanent or removable fashion.

An exhalation port 130 allows air to be purged from an interior space within the mask body during exhalation by a wearer. In an exemplary embodiment, exhalation port 130 is located centrally on mask body 120. An exhalation valve is fitted at the exhalation port to allow air to exit due to positive pressure created within mask body 120 upon exhalation, but prevent ingress of external air. In some exemplary embodiments, exhalation port 130 is positioned at a lower position on mask body 120, for example below the nose and mouth of a wearer.

A harness or other support (not shown) may be provided to support the mask in position about the nose and mouth of a wearer. In an exemplary embodiment, a harness is provided that includes one or more straps that pass behind a wearer's head. In some embodiments, straps may be attached to a crown member supported on a wearer's head, a suspension for a hard hat, or another head covering.

The one or more inlet ports of mask body 120 are configured to receive one or more breathing air source components. In an exemplary embodiment including two or more breathing air source components, as shown in FIG. 1a, mask body 120 includes first and second inlet ports 103, 104 on either side of mask body 120, and may be proximate cheek portions of mask body 120. First and second inlet ports 103, 104 include complementary mating features (not shown) such that first and second breathing air source components 101, 102 may be securely attached to mask body 120. Other suitable connections may be provided as known in the art. The mating features may result in a removable connection such that the breathing air source components 101, 102 may be removed and replaced at the end of service life of the breathing air source component or if use of a different breathing air source component is desired. Alternatively, the connection may be permanent such that the breathing air source components cannot be removed without damage to the breathing air source component, for example.

Respiratory protection device 100 includes a shut-off valve 150 for closing a fluid intake communication component. In an exemplary embodiment, shut-off valve 150 is operable between a closed position and an open position. In a closed position, shut-off valve 150 prevents fluid communication between each of one or more breathing air source components, such as filter cartridge 101 and/or 102, and a breathable air zone of mask body 120.

Shut-off valve 150 allows a wearer to perform a negative pressure fit check to provide an indication of the presence of leaks around a periphery of the mask body. When shut-off valve 150 is in a closed position, air is prevented from entering a breathable air zone of mask body 120. Inhalation by a wearer while the shut-off valve is in a closed position will result in a negative pressure within the mask, and in an exemplary embodiment may cause greater difficulty for a wearer to inhale or cause a compliant face contacting member to deflect inward, if an adequate seal has been achieved between the mask body and the wearer's face. If an adequate seal is not achieved, inhalation may result in air from the external environment entering the breathable air zone between the periphery of the mask body and the face of the wearer. In this way, a negative pressure fit check can be easily performed by a wearer wearing respiratory protection device 100 to determine if an adequate seal is achieved between the respiratory protection device 100 and the face and/or head of the wearer.

Figure 1B:
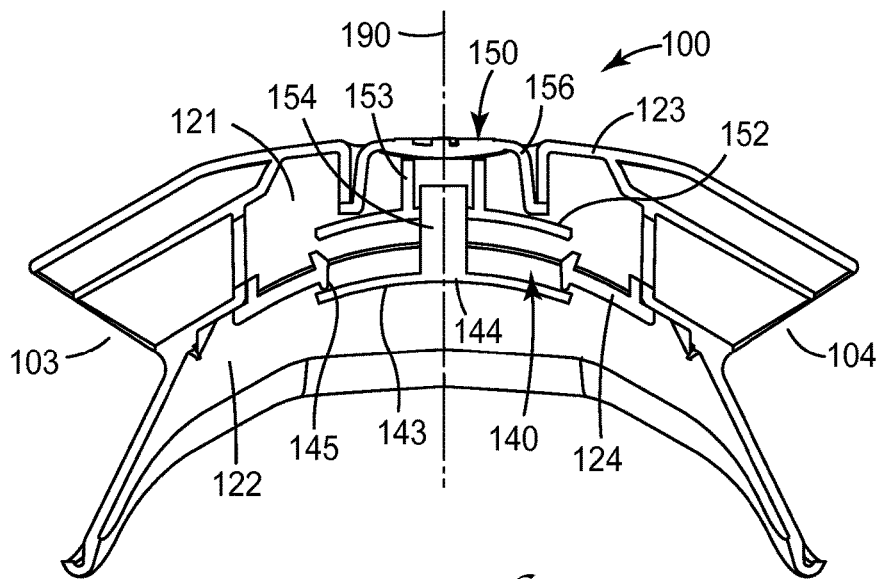
FIG. 1b is a partial cross-sectional view of an exemplary respiratory protection device according to the present disclosure.

FIG. 1b shows a representative cross-sectional view of an exemplary mask body 120 through a middle portion of mask body 120. Exemplary mask body 120 includes a first chamber 121 and a second chamber 122. A breathable air zone is defined by second chamber 122. In some embodiments, first and second breathing air source components 101, 102, such as filter cartridges, may be attached to first and second inlet ports 103, 104. First and second inlet ports 103, 104 are in fluid communication with first chamber 121. Accordingly, air entering mask body 120 through first inlet port 103 after passing through first breathing air source component 101 is in communication with air entering mask body 120 through second inlet port 104 after passing through second breathing air source component 102. Air from first and second breathing air sources 101, 102 is thus allowed to mix in first chamber 121 before being delivered to the breathable air zone defined by second chamber 122 of mask body 120.

In an exemplary embodiment, first and second chambers 121, 122 are separated by an inner wall 124 having a fluid intake communication component 140. Fluid intake communication component 140 comprises one or more openings to provide fluid communication between first and second chambers 121, 122. Fluid intake communication component 140 may include an inhalation valve for selectively allowing fluid communication between first and second chambers 121, 122, as described in greater detail below.

First chamber 121 is defined by one or more walls of mask body 120 and may exhibit any desired shape. In an exemplary embodiment, first chamber 121 is defined in part by an outer wall 123 that is an outer wall of mask body 120, and an inner wall 124. First chamber 121 is substantially sealed from the external environment with the exception of one or more inlet ports, such as first and second inlet ports 103, 104 extending through outer wall 123.

A chamber defined, at least in part, by the walls of mask body 120 and integrally formed with mask body 120, or rigid or semi-rigid portion 120a, provides a chamber within the structure of mask body 120 that may be configured to minimize extra bulk or weight that can be associated with a chamber separate from a mask body. Further, a chamber can be provided in close proximity to the head of a wearer such that the profile of the respiratory protection device is not greatly increased, minimizing a large moment of inertia away from the head of a wearer that could be perceived to cause neck pain or other discomfort for a wearer.

Second chamber 122 is similarly defined by one or more walls of mask body 120 and may exhibit any suitable shape defining a breathable air zone about the nose and mouth of a wearer. In an exemplary embodiment, second chamber 122 is defined in part by inner wall 124, a portion of outer wall 123, and, when respiratory protection device 100 is positioned for use on a wearer, a portion of a wearer's face and/or head. In various embodiments, inner wall 124 separates an interior space defined by outer wall 123 into first chamber 121 and second chamber 122, including a portion of outer wall 123 in front of inner wall 124 partially defining the first chamber 121, and a portion of outer wall 123 nearer to the face of a wearer partially defining the second chamber 122.

In an exemplary embodiment, first chamber 121 may function as a duct to direct air from one or more inlet ports, such as first and/or second inlet ports 103, 104, for example, to a different location in mask body 120. While many traditional respiratory masks deliver clean air from a cartridge through an inlet port and into the mask body at the location of the inlet port, first chamber 121 allows one or more inlet ports 103, 104 to be positioned generally independent of fluid intake communication component 140. In an exemplary embodiment, inlet ports 103, 104 are positioned near cheek portions of mask body 120, and fluid intake communication component 140 is positioned centrally. For example, fluid intake communication component is positioned proximate a central axis extending through the mask and dividing mask body 120 into imaginary left and right halves, such as axis 190. Such a component may be said to be centrally positioned if some portions of the component are positioned on each side of axis 190. A configuration in which one or more inlet ports 103, 104 are positioned near cheek portions while a fluid intake communication component 140 is centrally located may allow a breathing air source component to be received in a desirable position and/or orientation, for example extending rearwardly along the face of a wearer so as to minimize obstruction to the field of view or maintain the center of mass of the cartridge in close proximity to the mask body 120 and/or face of the wearer. Fluid intake communication component 140, however, may still be positioned centrally so as to deliver clean air in close proximity to the nose and mouth of a wearer, and in an exemplary embodiment is provided at an upper central location. Thus, first chamber 121 allows first and second breathing air source components to be positioned to provide desired ergonomic characteristics, and allows fluid intake communication component 140 to be positioned to provide desirable airflow to the wearer, for example. Further, first chamber 121 allows first and second inlet ports to be in fluid communication with a single fluid intake communication component. A respiratory protection device having two or more breathable air source components and a single fluid intake communication component can reduce manufacturing costs and provide a more robust respiratory protection device. Costly fluid intake communication components can be minimized, and the use of relatively fragile diaphragms or flaps may be reduced.

Figure 1C:
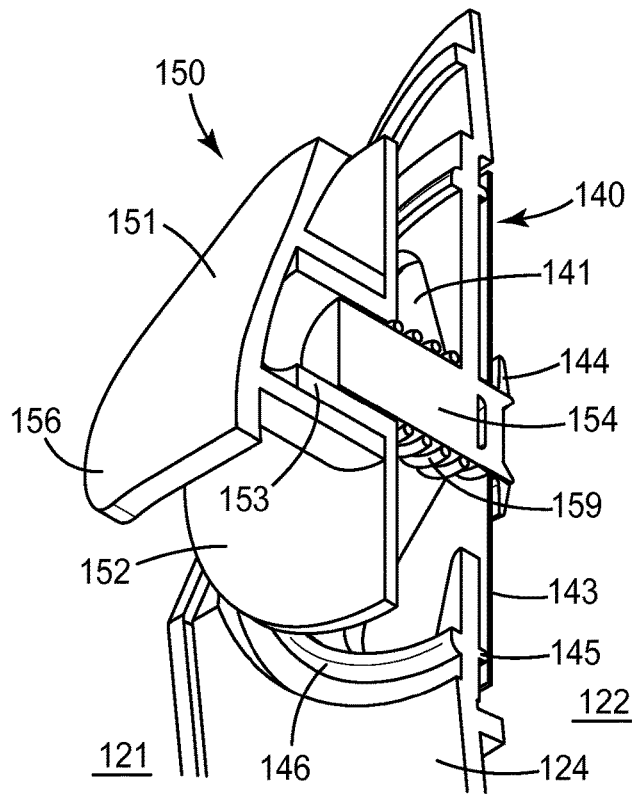
FIG. 1c is a partial cross-sectional perspective view of an exemplary respiratory protection device according to the present disclosure showing a shut-off valve in an open position.
Figure 1D:
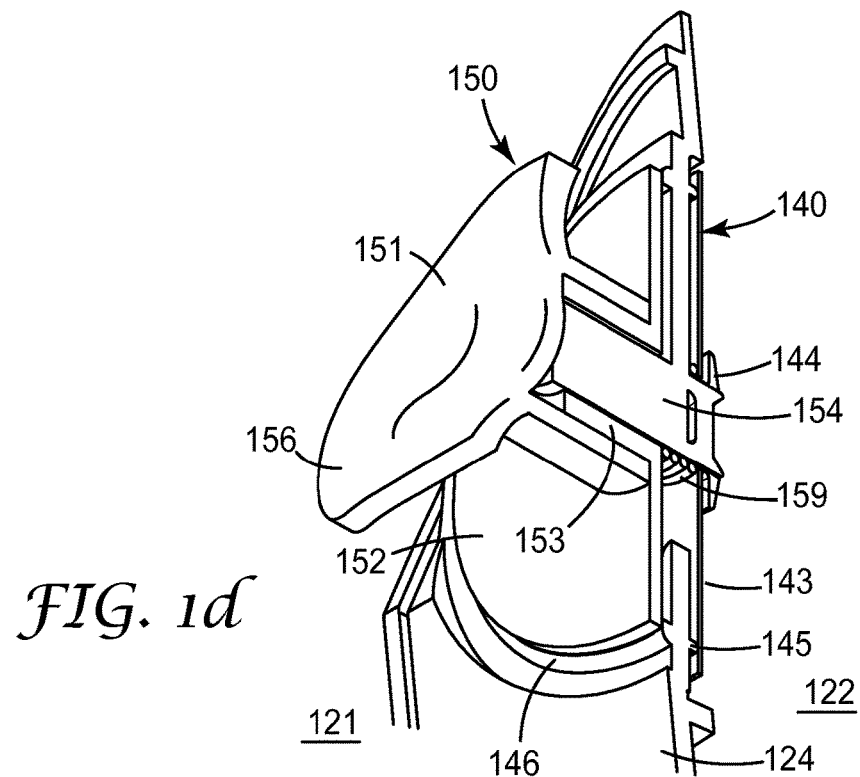
FIG. 1d is a partial cross-sectional perspective view of an exemplary respiratory protection device according to the present disclosure showing a shut-off valve in a closed position.

FIGS. 1c and 1d provide partial cross-sectional views showing an exemplary shut-off valve 150 of respiratory protection device 100. As described above, mask body 120 includes first and second chambers 121 and 122 separated by inner wall 124. In an exemplary embodiment, inner wall 124 includes a fluid intake communication component 140 including an inhalation port 141 to allow fluid communication between first chamber 121 and second chamber 122. Fluid intake communication component 140 allows air to be drawn into second chamber 122 from the first chamber 121 during inhalation but prohibits air from passing from second chamber 122 into first chamber 121. In an exemplary embodiment, fluid intake communication component 140 includes a diaphragm or flap 143. The diaphragm or flap 143 may be secured at a central location 144 by one or more central pins or flanges, for example, or at a peripheral edge or another suitable location as known in the art. In the absence of negative pressure within second chamber 122 of mask body 120, such as when a wearer is exhaling for example, the diaphragm is biased towards a surface of fluid intake communication component, such as sealing ring 145. During inhalation by a wearer, negative pressure within second chamber 122, i.e. a pressure lower than the pressure of the external atmosphere, may result in diaphragm or flap 143 being in an open position to allow air to enter second chamber 122 from first chamber 121. That is, diaphragm or flap 143 flexes or moves away from sealing ring 145 such that air may pass into second chamber 122 to be inhaled by a wearer. In various exemplary embodiments, fluid intake communication component 140 may include multiple inhalation ports and/or two or more diaphragms or flaps 143 to selectively allow fluid communication from first chamber 121 to second chamber 122 when pressure in second chamber 122 is negative.

In an exemplary embodiment, shut-off valve 150 of mask body 120 includes an actuator 151 and sealing pad 152. In a closed position, sealing pad 152 contacts inner wall 124 to block inhalation port 141 to prevent fluid communication between the two or more breathing air sources and the breathable air zone defined by second chamber 122. When shut-off valve 150 is in a closed position, air from breathing air source components 101, 102 is in fluid communication with first chamber 121 but is prevented from entering the breathable air zone defined by second chamber 122 through fluid intake communication component 140. In an exemplary embodiment, sealing pad 152 contacts a sealing surface 146 surrounding inhalation port 141. Sealing surface 146 may be in the form of a ridge or projection extending outwardly from inner wall 124 to allow an adequate seal to be achieved around a periphery of inhalation port 141.

Sealing pad 152 may be formed of a soft or resilient material such that sealing pad may flex upon contacting sealing surface 146. In an exemplary embodiment, sealing pad 152 includes seating features, such as angled or flanged lips (not shown), to facilitate an adequate seal with sealing surface 146. All or a portion of sealing pad 152 may also articulate or rotate when contacting sealing surface 146. A sealing pad that may flex and/or articulate or rotate may facilitate formation of an adequate seal around inhalation port 141.

In an exemplary embodiment, a shaft 154 guides sealing pad 152 and maintains sealing pad 152 in proper alignment with inhalation port 141 as sealing pad 152 moves linearly between open and closed positions. Sealing pad 152 may include a boss, flange, or other projection 153 that further serves to prevent rotation or misalignment of sealing pad 152. Shaft 154 extends from inner wall 124, such as from a central portion of fluid intake communication component 140. In various other exemplary embodiments, shaft 154 may extend from other portions of mask body 120, for example.

Shut-off valve 150 may be operated to switch between an open position (FIG. 1c) and a closed position (FIG. 1d). In an exemplary embodiment, actuator 151 is a button, such as an over-molded elastomeric push-button, slideable button, or the like, that may be pressed inward linearly to cause sealing pad 152 to move towards fluid intake communication component 140 until sealing pad 152 contacts sealing surface 146. In an open position shown in FIG. 1c, air may pass through inhalation port 141 into the breathable air zone defined by second chamber 122 if allowed by diaphragm or flap 143. In a closed position shown in FIG. 1d, sealing pad 152 is in sealing engagement with sealing surface 146 to prevent air from passing through inhalation port 141. When actuator 151 is released by a wearer, actuator 151 returns to an open position due to a resilient member that biases sealing pad 152 away from sealing engagement with sealing surface 146.

In an exemplary embodiment, an actuator 151 in the form of an elastomeric button acts as a resilient member that biases sealing pad towards an open position away from sealing engagement with sealing surface 146 in the absence of an applied force, for example. Actuator 151 may include a flexible web 156 attached to outer wall 123 (FIGS. 1a, 1b) of mask body 120 to support actuator 151 and/or bias shut-off valve 150 to an open position. The web is formed of a flexible or compliant material that is able to elastically deform when actuator 151 is pressed inwardly by a wearer, as shown in FIG. 1d, for example. In a closed position, flexible web 156 is flexed and/or deformed allowing sealing pad 152 to travel towards sealing surface 146. Flexure and/or deformation of flexible web 156 is desirably limited to the elastic regime such that flexible web 156 is able to repeatedly return to an original configuration in which shut-off valve 150 is in an open position.

Other resilient members may be provided in place of or in addition to a flexible web. In various exemplary embodiments, a coil spring, leaf spring, elastomeric band or other suitable resilient member as known in the art may be provided to bias actuator 151 and/or sealing pad 152 to an open position. Alternatively or in addition, a spring loaded member may be provided on a surface of sealing pad 152 to bias actuator 151, and shut-off valve 150, away from sealing surface 146 and towards an open position. In some exemplary embodiments, a coil spring 159 is provided around shaft 154 to bias actuator 151 and sealing pad 152 away from sealing surface 146 and into an open position. A coil spring may provide a force to bias actuator 151 and sealing pad 152 in place of or in addition to one or more additional resilient members, such as the elastomeric web described above.

In an exemplary embodiment, actuator 151 is attached to mask body 120 such that a seal is formed between actuator 151 and mask body 120, for example by over-molding the actuator on mask body 120. Other suitable seals may be provided using gaskets, flanges, adhesive, interference fits, molding techniques, sonic welding, and other suitable techniques as known in the art to provide an adequate seal such that air and contaminants from the external environment are unable to enter mask body 120 proximate actuator 151. The presence of an adequate seal preventing ingress of air and contaminants from the external environment is desirable because the volume surrounding the portions of shut-off valve 150 internal to mask body 120 is in fluid communication with breathable air zone 122. A sufficient seal proximate actuator 151 thus protects the breathability of air in breathable air zone 122 when shut-off valve 150 is in an open, closed, or intermediate position.

Fluid intake communication component 140 and shut-off valve 150 are configured to minimize a negative effect on pressure drop that could interfere with a wearer's ability to breathe freely. In various exemplary embodiments, sealing pad 152 is positioned between approximately 8 mm and 1 mm, approximately 6 mm and 2 mm, or approximately 3 mm from sealing surface 146 when shut-off valve 150 is in an open position. That is, sealing pad 152 travels between approximately 8 mm and 1 mm, or approximately 6 mm and 2 mm, or approximately 3 mm from an open position to a closed position. Such a distance provides a shut-off valve that may be relatively compact while providing sufficient space for air to pass through when in an open position.

In various exemplary embodiments, shut-off valve 150 may remain in a closed position due to a negative pressure within the mask. That is, while performing a negative pressure fit check, a wearer may move actuator 151 to a closed position by pressing inward on actuator 151, inhale, and then release actuator 151. After a wearer releases actuator 151, the resilient member may not overcome the negative pressure within second chamber 122 applied on sealing pad 152. Shut-off valve 150 may thus remain in a closed position until the wearer exhales or the pressure within second chamber 122 is no longer sufficient to overcome the force of the resilient member. A resilient member that allows shut-off valve 150 to remain in a closed position even after actuator 151 is released by a wearer may allow for a more accurate fit check because the wearer is not applying a force on actuator 151 that could affect the seal between mask body 120 and the wearer's face. However, even while the resilient member allows shut-off valve 150 to remain in a closed position due to negative pressure within a breathable air zone of mask body 120, the shut-off valve may automatically return to an open position without further input to actuator 151 by the wearer. An increase in pressure within the mask body, resulting from exhalation of the wearer, for example, may result in the shut-off valve 150 returning to an open position in which the wearer may breathe freely. Such a feature allows a wearer to safely breathe without further input to actuator 151 to return shut-off valve 150 to an open position.

In other exemplary embodiments, shut-off valve 150 may remain in a closed position regardless of pressure within second chamber 122 and may return to an open position upon further input by a wearer.

Figure 2A:
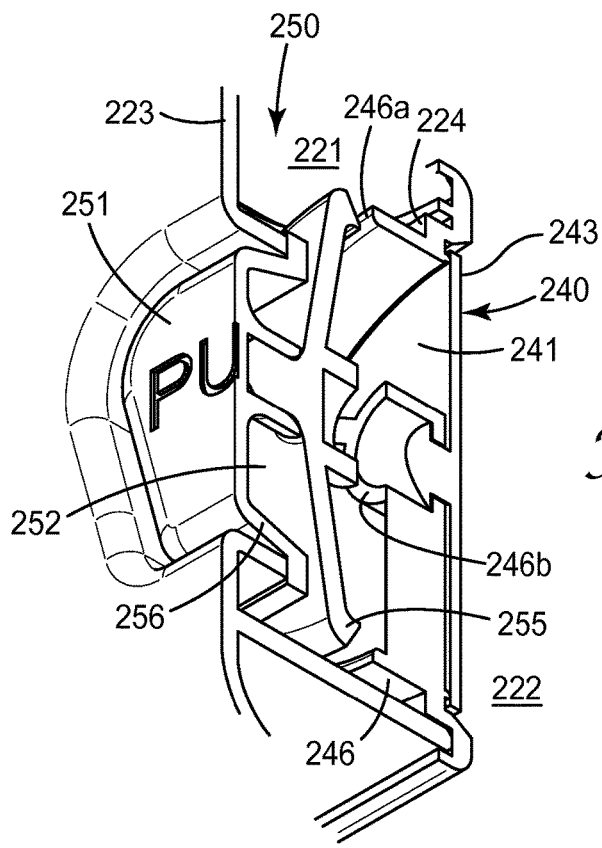
FIG. 2a is a partial cross-sectional perspective view of an exemplary respiratory protection device according to the present disclosure showing a shut-off valve in an open position.
Figure 2B:
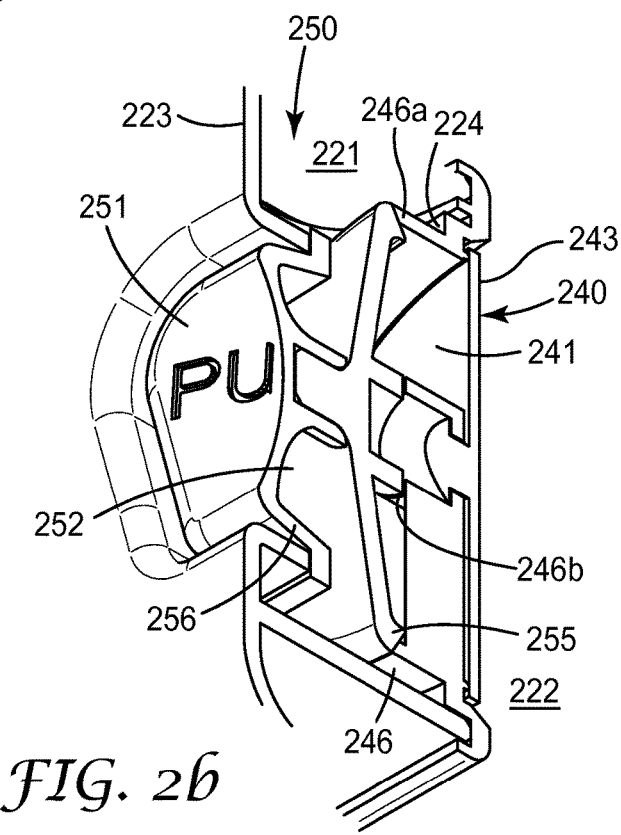
FIG. 2b is a partial cross-sectional perspective view of an exemplary respiratory protection device according to the present disclosure showing a shut-off valve in a closed position.

FIGS. 2a and 2b illustrate an exemplary embodiment of a shut-off valve 250 having a self-aligning sealing pad. In an exemplary embodiment, shut-off valve 250 includes an actuator 251 and sealing pad 252. In a closed position, sealing pad 252 contacts inner wall 224 to block inhalation port 241 to prevent fluid communication between the two or more breathing air sources and the breathable air zone defined by second chamber 222. When shut-off valve 250 is in a closed position, air from breathing air source components 201, 202 (not shown) is in fluid communication with first chamber 221 but is prevented from entering the breathable air zone defined by second chamber 222 through fluid intake communication component 240. In an exemplary embodiment, sealing pad 252 contacts a sealing surface 246 surrounding inhalation port 241. Sealing surface 246 may be in the form of a ridge or projection extending outwardly from inner wall 224 to allow an adequate seal to be achieved around a periphery of inhalation port 241. In an exemplary embodiment, sealing surface 246 includes a first sealing surface portion 246a surrounding an outer periphery of inhalation port 241 and a second sealing surface portion 246b surrounding an inner periphery of inhalation port 241.

Sealing pad 252 may be formed of a soft or resilient material such that sealing pad 252 may flex upon contacting sealing surface 246. In an exemplary embodiment, sealing pad 252 includes seating features 255, such as angled or flanged lips, to facilitate an adequate seal with sealing surface 246. All or a portion of sealing pad 252 may also articulate or rotate when contacting sealing surface 246. A sealing pad that may flex and/or articulate or rotate may facilitate formation of an adequate seal around inhalation port 241.

In an exemplary embodiment, sealing pad 252 is attached to and supported by actuator 251. Rather than traveling on a shaft projecting from fluid intake communication component 240, for example, sealing pad 252 is guided by actuator 251. In some exemplary embodiments, sealing pad 252 and actuator 251 may be integrally formed as a unitary component. Seating features 245 facilitate an appropriate alignment and/or adequate seal with sealing surface 246. In some embodiments, seating features 245 may include complementary features to align sealing pad 252 with sealing surface 246.

Shut-off valve 250 may be operated to switch between an open position (FIG. 2a) and a closed position (FIG. 2b). In an exemplary embodiment, actuator 251 is a button, such as an over-molded elastomeric push-button, slideable button, or the like, that may be pressed inward by a wearer to cause sealing pad 252 to move towards fluid intake communication component 240 until sealing pad 252 contacts sealing surface 246. In an open position shown in FIG. 2a, air may pass through inhalation port 241 into the breathable air zone defined by second chamber 222 if allowed by diaphragm or flap 243. In a closed position shown in FIG. 2b, sealing pad 252 is in sealing engagement with sealing surface 246 to prevent air from passing through inhalation port 241. At least a portion of sealing pad 252 is flexed and/or compressed due to the force applied to actuator 251, and such flexure and/or compression may facilitate an adequate seal. When actuator 251 is released by a wearer, actuator 251 may return to an open position due to a resilient member that biases sealing pad 252 away from sealing engagement with sealing surface 246. In some exemplary embodiments, as described above with respect to shut-off valve 150 for example, shut-off valve 250 may remain in a closed position due to a negative pressure within the mask until the wearer exhales or the pressure within second chamber 222 is no longer greater than the force of the resilient member.

In an exemplary embodiment, an actuator 251 in the form of an elastomeric button acts as a resilient member that biases sealing pad 252 towards an open position away from sealing engagement with sealing surface 246. Actuator 251 may include a flexible web 256 attached to outer wall 223 of mask body 220 to support actuator 251 and/or bias shut-off valve 250 to an open position. Flexible web 256 is formed of a flexible or compliant material that is able to elastically deform when actuator 251 is pressed inwardly by a wearer. In a closed position, flexible web 256 is flexed and/or deformed allowing sealing pad 252 to travel towards sealing surface 246. Flexure and/or deformation of flexible web 256 is desirably limited to the elastic regime such that flexible web 256 is able to repeatedly return to an original configuration in which the shut-off valve is in an open position.

Other resilient members may be provided in place of or in addition to flexible web 256. In various exemplary embodiments, a coil spring, leaf spring, elastomeric band, or other suitable resilient member as known in the art may be provided to bias actuator 251 and sealing pad 252, to an open position. Alternatively or in addition, a spring loaded member may be provided on a surface of sealing pad 252 to bias actuator 251, and shut-off valve 250, away from sealing surface 246 and into an open position.

Figure 3A:
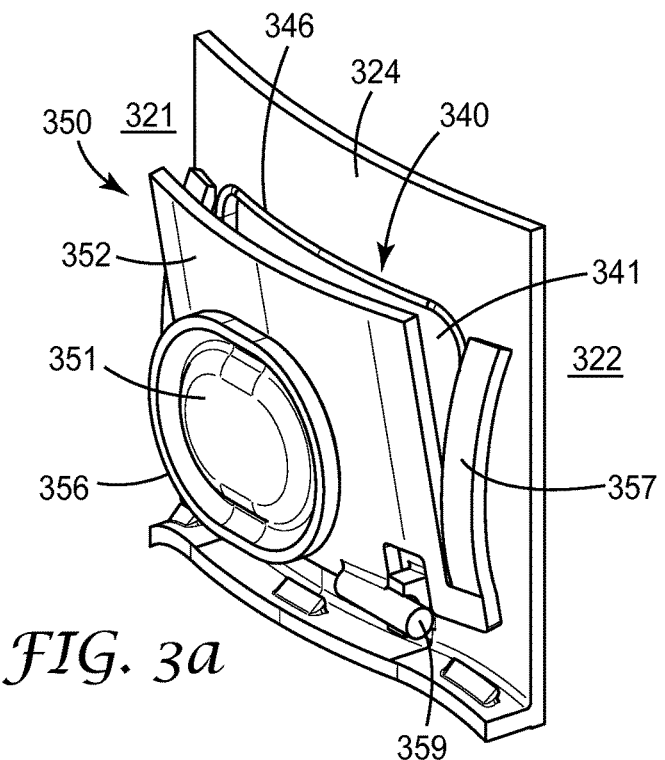
FIG. 3a is a partial perspective view of an exemplary respiratory protection device according to the present disclosure showing a shut-off valve in an open position.
Figure 3B:
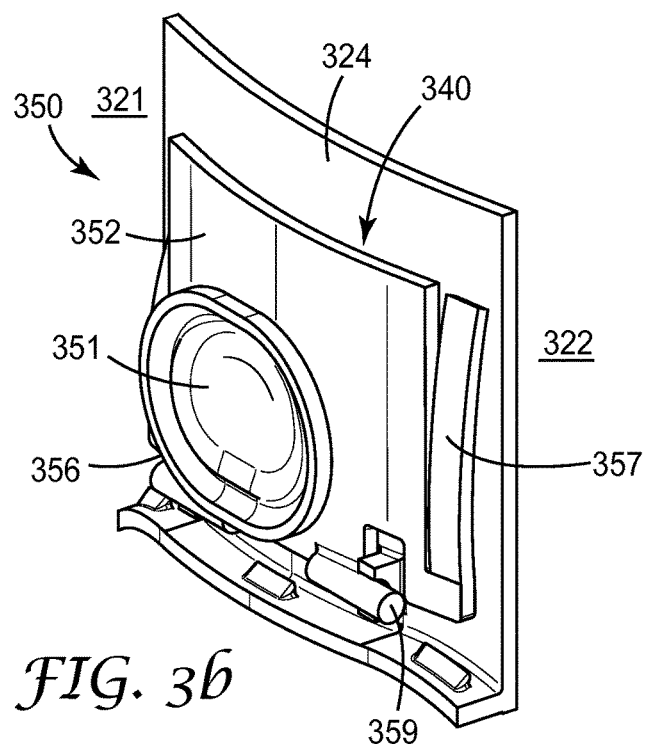
FIG. 3b is a partial perspective view of an exemplary respiratory protection device according to the present disclosure showing a shut-off valve in a closed position.

FIGS. 3a and 3b illustrate an exemplary embodiment of a shut-off valve 350 having a pivoting sealing pad. In an exemplary embodiment, shut-off valve 350 includes an actuator 351 and sealing pad 352. Similar to respiratory protection device 100 described above with reference to FIGS. 1a through 1d, shut-off valve 350 may be incorporated in a respiratory protection device including a first chamber 321 and a breathable air zone defined by a second chamber 322, for example. In an exemplary embodiment, first and second chambers 321, 322 are separated by an inner wall 324 including a fluid intake communication component 340. Fluid intake communication component 340 comprises one or more openings to provide fluid communication between first and second chambers 321, 322. Fluid intake communication component 340 may include an inhalation valve for selectively allowing fluid communication between first and second chambers 321, 322. In an exemplary embodiment, fluid intake communication component 340 includes a diaphragm or flap (not shown) such that air may be drawn into the second chamber from the first chamber during inhalation but prohibits air from passing from the second chamber into the first chamber, as described above with reference to fluid intake communication component 140 for example.

In an exemplary embodiment, shut-off valve 350 includes an actuator 351 and sealing pad 352. In a closed position, sealing pad 352 contacts inner wall 324 to block inhalation port 341 to prevent fluid communication between the two or more breathing air sources and the breathable air zone defined by second chamber 322. When shut-off valve 350 is in a closed position, air from breathing air source components (not shown) is in fluid communication with first chamber 321 but is prevented from entering the breathable air zone defined by second chamber 322 through fluid intake communication component 340. In an exemplary embodiment, sealing pad 352 contacts a sealing surface 346 surrounding inhalation port 341. Sealing surface 346 may be in the form of a ridge or projection extending outwardly from inner wall 324 to allow an adequate seal to be achieved around a periphery of inhalation port 341.

Shut-off valve 350 may be operated to switch between an open position (FIG. 3a) and a closed position (FIG. 3b). In an exemplary embodiment, actuator 351 is a button, such as an over-molded elastomeric push-button, slideable button, or the like, that may be pressed inward by a wearer to cause sealing pad 352 to pivot at pivot location 359 until sealing pad 352 contacts sealing surface 346. In an open position shown in FIG. 3a, air may pass through inhalation port 341 into the breathable air zone defined by second chamber 322 if allowed by a diaphragm or flap, for example. In a closed position shown in FIG. 3b, sealing pad 352 is in sealing engagement with sealing surface 346 to prevent air from passing through inhalation port 341. At least a portion of sealing pad 352 may be flexed and/or compressed due to the force applied to actuator 351, and such flexure and/or compression facilitates an adequate seal. When actuator 351 is released by a wearer, actuator 351 may return to an open position due to a resilient member that biases actuator 351 to an open position. In some exemplary embodiments, as described above with respect to shut-off valve 150 for example, shut-off valve 350 may remain in a closed position due to a negative pressure within the mask until the wearer exhales or the pressure within second chamber 322 is no longer greater than the force of the resilient member.

In an exemplary embodiment, an actuator 351 in the form of an elastomeric button acts as a resilient member that biases sealing pad 352 towards an open position away from sealing engagement with sealing surface 346. Actuator 351 may include a flexible web 356 attached to an outer wall (not shown) of mask body 320 to support actuator 351 and/or bias shut-off valve 350 to an open position. Web 356 is formed of a flexible or compliant material that is able to elastically deform when actuator 351 is pressed inwardly by a wearer, as shown in FIG. 3b, for example. In some exemplary embodiments, actuator 351 is not attached to sealing pad 352. A resilient member such as flexible web 356 biases actuator 351 to an open position and one or more additional members, such as spring member 357 biases sealing pad 352 to an open position. Spring member 357 may comprise any suitable spring to bias sealing pad 352 to an open position including a coil spring, leaf spring, elastomeric band, or suitable resilient member as known in the art. In other exemplary embodiments, actuator 351 is attached to sealing pad 352 and a resilient member such as a flexible web and/or spring member 357 bias both actuator 351 and sealing pad 352 towards an open position.

Sealing pad 352 may include at least a portion of soft or resilient material such that at least a portion of sealing pad 352 may flex or compress upon contacting sealing surface 346. At least a portion of sealing pad 352 may be rigid or semi-rigid such that force from actuator 351 may be transmitted to the entire portion of sealing pad 352 that contacts sealing surface 346. Excessive flexure of sealing pad 352 when actuator 351 moves sealing pad 352 into a closed position could result in gaps between sealing pad 352 and sealing surface 346 that could allow ingress of air inhibiting performance of an accurate negative pressure fit check.

Figure 4A:
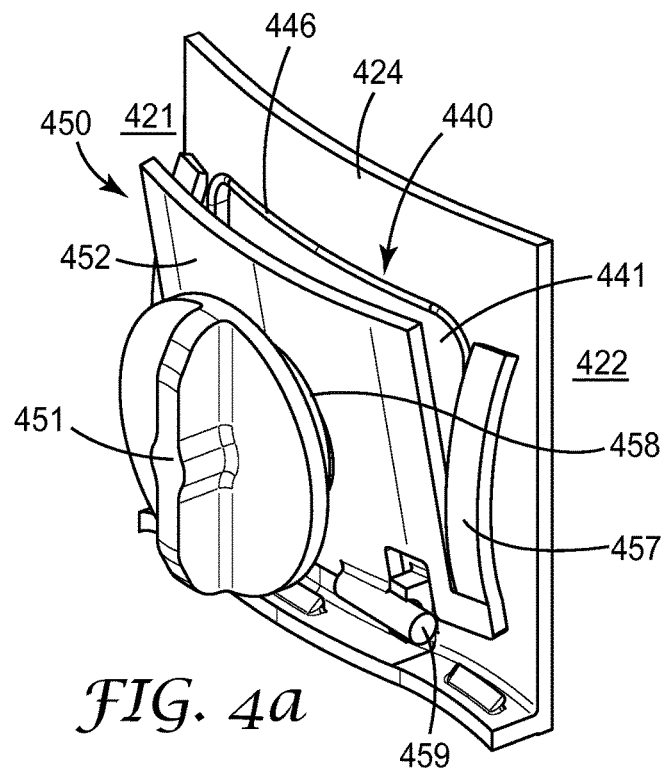
FIG. 4a is a partial perspective view of an exemplary respiratory protection device according to the present disclosure showing a shut-off valve in an open position.
Figure 4B:
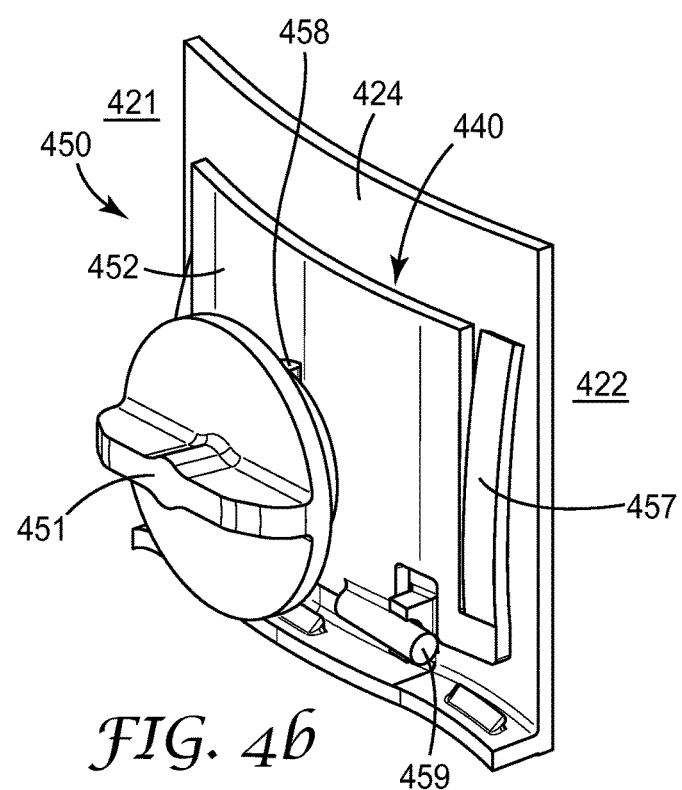
FIG. 4b is a partial perspective view of an exemplary respiratory protection device according to the present disclosure showing a shut-off valve in a closed position.

FIGS. 4a and 4b illustrate an exemplary embodiment of a shut-off valve 450 having a pivoting sealing pad and a rotatable actuator. Similar to respiratory protection device 100 described above with reference to FIGS. 1a through 1d, shut-off valve 450 may be incorporated in a respiratory protection device including a first chamber 421 and a breathable air zone defined by a second chamber 422, for example. In an exemplary embodiment, first and second chambers 421, 422 are separated by an inner wall 424 including a fluid intake communication component 440. Fluid intake communication component 440 comprises one or more openings to provide fluid communication between first and second chambers 421, 422. Fluid intake communication component 440 may include an inhalation valve for selectively allowing fluid communication between first and second chambers 421, 422. In an exemplary embodiment, fluid intake communication component 440 includes a diaphragm or flap (not shown) such that air may be drawn into the second chamber from the first chamber during inhalation but prohibits air from passing from the second chamber into the first chamber, as described above with reference to fluid intake communication component 140 for example.

In an exemplary embodiment, shut-off valve 450 includes a rotatable actuator 451 and sealing pad 452. In a closed position, sealing pad 452 contacts inner wall 424 to block inhalation port 441 to prevent fluid communication between the two or more breathing air sources and the breathable air zone defined by second chamber 422. When shut-off valve 450 is in a closed position, air from breathing air source components (not shown) is in fluid communication with first chamber 421 but is prevented from entering the breathable air zone defined by second chamber 422 through fluid intake communication component 440. In an exemplary embodiment, sealing pad 452 contacts a sealing surface 446 surrounding inhalation port 441. Sealing surface 446 may be in the form of a ridge or projection extending outwardly from inner wall 424 to allow an adequate seal to be achieved around a periphery of inhalation port 441.

Shut-off valve 450 may be operated to switch between an open position (FIG. 4a) and a closed position (FIG. 4b). In an exemplary embodiment, actuator 451 is a rotatable actuator that may be rotated between a first position and a second position. When rotatable actuator 451 is in a first position, shut-off valve 450 is in an open position, and when rotatable actuator 451 is in a second position, shut-off valve 450 is in a closed position. In an exemplary embodiment, rotatable actuator 451 is rotated 90 degrees between an open position and a closed position. In other exemplary embodiments rotatable actuator 451 is rotated 45 degrees, 180 degrees, or other suitable angle, between an open position and a closed position. Rotatable actuator 451 includes a cam 458. Rotation of rotatable actuator 451 causes cam 458 to push sealing pad 452 towards sealing surface 446 and pivot at pivot location 459 until sealing pad 452 contacts sealing surface 446. In a closed position shown in FIG. 4b, sealing pad 452 is in sealing engagement with sealing surface 446 to prevent air from passing through inhalation port 441. At least a portion of sealing pad 452 may be flexed and/or compressed due to the force applied to actuator 451, and such flexure and/or compression facilitates an adequate seal. In an exemplary embodiment, rotatable actuator 451 returns to an open position due to a resilient member (not shown) when rotatable actuator is released by a wearer. Resilient member may be a torsion spring, for example, or other suitable resilient member as known in the art. In other exemplary embodiments, rotatable actuator 451 returns to an open position only upon further input by a wearer and remains in the second position, such that shut-off valve 450 is in a closed position, until the wearer rotates actuator 451 to the first position for example. A spring member 457 biases sealing pad 452 to an open position. Spring member 457 may comprise any suitable spring to bias sealing pad 452 to an open position including a coil spring, leaf spring, elastomeric band or suitable resilient member as known in the art.

Sealing pad 452 may include at least a portion of soft or resilient material such that at least a portion of sealing pad 452 may flex or compress upon contacting sealing surface 446. At least a portion of sealing pad 452 may be rigid or semi-rigid such that force from actuator 451 may be transmitted to the entire portion of sealing pad 452 that contacts sealing surface 446. A rotatable actuator 451 able to rotate through a predetermined angle between an open and closed position and having a cam 458 that causes sealing pad 452 to move to a closed position results in a uniform force transmitted to sealing pad 452 each time sealing pad 452 is moved to a closed position. Thus, an appropriate force to create a desired seal is easily and consistently achieved.

A rotatable actuator is believed to provide several advantages including ease of use and less effect on the fit of a mask body during performance of a negative pressure fit check. Rotation of a rotatable actuator does not require force in a direction towards the face of a wearer and thus may not alter the natural contact between a mask body and a wearer's face. Accordingly, an accurate negative pressure fit check may be achieved.

Figure 5A:
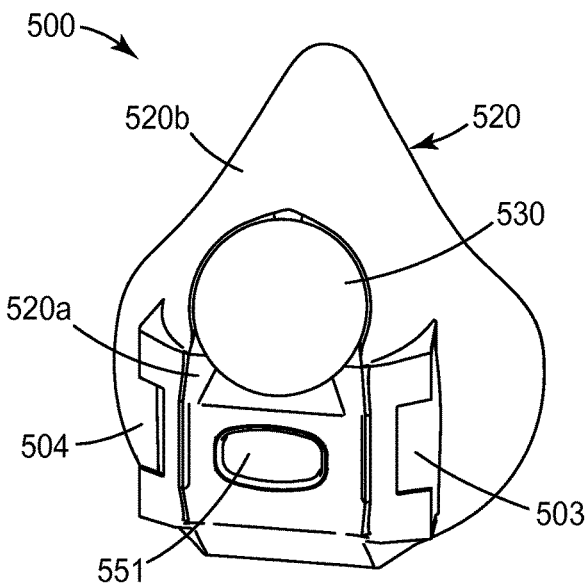
FIG. 5a is a front perspective view of an exemplary respiratory protection device according to the present disclosure.
Figure 5B:
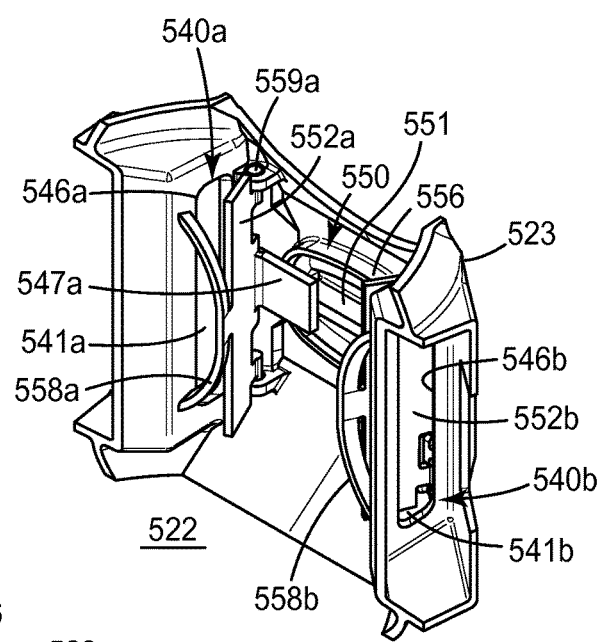
FIG. 5b is a partial perspective view of an exemplary respiratory protection device according to the present disclosure showing a shut-off valve in an open position.
Figure 5C:
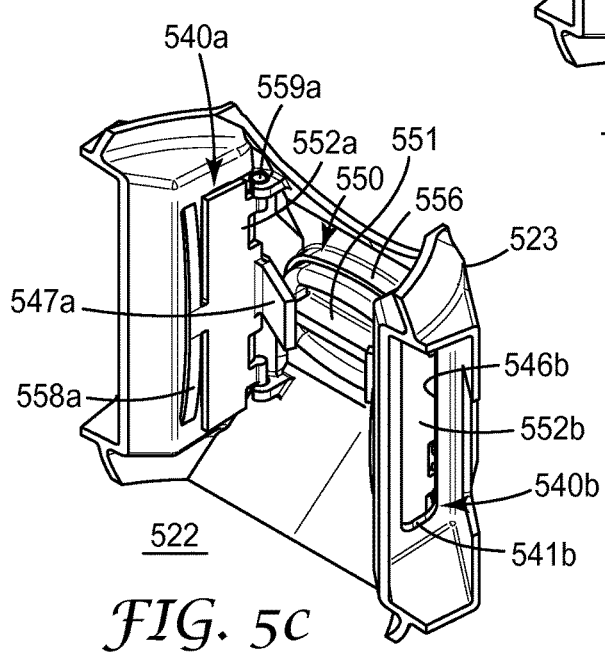
FIG. 5c is a partial perspective view of an exemplary respiratory protection device according to the present disclosure showing a shut-off valve in a closed position.

FIGS. 5a through 5c illustrate an exemplary respiratory protection device 500 that may cover the nose and mouth and provide breathable air to a wearer. The respiratory protection device 500 includes a mask body 520 including first and second inlet ports 503 and 504. First and second breathing air source components (not shown) may be positioned on opposing sides of mask body 520. In an exemplary embodiment, first and second breathing air source components are filter cartridges configured to be attached at first and second inlet ports 503 and 504. The filter cartridges filter air received from the external environment before the air passes into interior space within the mask body for delivery to a wearer.

The mask body 520 may include a rigid or semi-rigid portion 520a and a compliant face contacting portion 520b. The compliant face contacting portion of the mask body is compliantly fashioned for allowing the mask body to be comfortably supported over a person's nose and mouth and/or for providing an adequate seal with the face of a wearer to limit undesirable ingress of air into an interior of mask body 520, for example. The face contacting member 520b may have an inturned cuff so that the mask can fit comfortably and snugly over the wearer's nose and against the wearer's cheeks. The rigid or semi-rigid portion 520a provides structural integrity to mask body 520 so that it can properly support breathing air source components, such as filter cartridges, for example. In various exemplary embodiments, mask body portions 520a and 520b may be provided integrally or as separately formed portions that are subsequently joined together in permanent or removable fashion.

An exhalation port 530 allows air to be purged from an interior space within the mask body during exhalation by a wearer. In an exemplary embodiment, exhalation port 530 is located centrally on mask body 520. An exhalation valve is fitted at the exhalation port to allow air to exit due to positive pressure created within mask body 520 upon exhalation, but prevent ingress of external air.

First and second inlet ports 503, 504 are configured to receive first and second breathing air source components. In an exemplary embodiment shown in FIG. 5a, mask body 520 includes first and second inlet ports 503, 504 on either side of mask body 520, and may be proximate cheek portions of mask body 520. First and second inlet ports 503, 504 include complementary mating features such that first and second breathing air source components (not shown) may be securely attached to mask body 520. Other suitable connections may be provided as known in the art. The mating features may result in a removable connection such that the breathing air source components may be removed and replaced at the end of service life of the breathing air source component or if use of a different breathing air source component is desired. Alternatively, the connection may be permanent such that the breathing air source components cannot be removed without damage to the breathing air source component, for example.

Respiratory protection device 500 includes a shut-off valve 550 for closing multiple fluid intake communication components. In an exemplary embodiment, shut-off valve 550 is operable between a closed position and an open position. In a closed position, shut-off valve 550 prevents fluid communication between both of breathing air source components at inlet ports 503 and 504 and a breathable air zone of mask body 520.

Shut-off valve 550 allows a wearer to perform a negative pressure fit check to provide an indication of the presence of leaks around a periphery of the mask body. When shut-off valve 550 is in a closed position, air is prevented from entering a breathable air zone of mask body 520. Inhalation by a wearer while the shut-off valve is in a closed position will result in a negative pressure within the mask, and in some exemplary embodiments may cause a compliant face contacting member to deflect inward, if an adequate seal has been achieved between the mask body and the wearer's face. If an adequate seal is not achieved, inhalation may result in air from the external environment entering the breathable air zone between the periphery of the mask body and the face of the wearer. In this way, a negative pressure fit check can be easily performed by a wearer wearing respiratory protection device 500 to determine if an adequate seal is achieved between the respiratory protection device 500 and the face and/or head of the wearer.

First and second breathing air source components, such as filter cartridges, may be attached to first and second inlet ports 503, 504. Accordingly, air entering mask body 520 through first inlet port 503 after passing through a first breathing air source component may enter breathable are zone 522 through first fluid intake communication component 540a, and air entering mask body 520 through second inlet port 504 after passing through a second breathing air source component may enter breathable are zone 522 through second fluid intake communication component 540b. Air from first and second breathing air sources 501, 502 thus enter breathable air zone 522 through distinct fluid intake communication components 540a, 540b. Each of the first and second fluid intake communication components 540a, 540b comprise one or more openings to provide fluid communication between first and second inlet ports 503, 504 and breathable air zone 522. First and second fluid intake communication components 540a, 540b may each include an inhalation valve for selectively allowing fluid communication between first and second inlet ports 503, 504 and breathable air zone 522.

In an exemplary embodiment, shut-off valve 550 includes an actuator 551 and first and second sealing pads 552a, 552b. When the actuator is depressed, first and second sealing pads 552a, 552b block the first and second inhalation ports to prevent fluid communication between the two or more breathing air sources and the breathable air zone 522. In an exemplary embodiment, first and second sealing pads 552a, 552b include actuation surfaces 547a, 547b contacted by actuator 551 to cause sealing pads 552a, 552b to block first and second inhalation ports. In an exemplary embodiment, sealing pads 552a, 552b contact first and second sealing surfaces 546*a*, 546*b* surrounding first and second inhalation ports 541*a*, 541*b*, respectively. Sealing surfaces 546*a*, 546*b* may be in the form of a ridge or projection extending outwardly from an inner surface of mask body 520 or first and second fluid intake communication components 540*a*, 540*b* to allow an adequate seal to be achieved around a periphery of inhalation ports 541*a* and 541*b*.

Shut-off valve 550 may be operated to switch between an open position (FIG. 5*b*) and a closed position (FIG. 5*c*). In an exemplary embodiment, actuator 551 is a button, such as an over-molded elastomeric push-button, slideable button, or the like, that may be pressed inward by a wearer to cause first and second sealing pads 552*a*, 552*b* to pivot about pivot locations 559*a*, 559*b* (not shown) until first and second sealing pads 552*a*, 552*b* contact sealing surfaces 546*a*, 546*b* of first and second fluid intake communication components 540*a*, 540*b*. In an open position shown in FIG. 5*b*, air may pass through inhalation ports 541*a*, 541*b* into the breathable air zone 522 if allowed by a diaphragm or flap (not shown). In a closed position shown in FIG. 5*c*, sealing pad 552*a* is in sealing engagement with sealing surface 546*a* to prevent air from passing through inhalation port 541*a*. When actuator 551 is released by a wearer, actuator 551 returns to an open position due to a resilient member that biases actuator 551 to an open position. In some exemplary embodiments, as described above with respect to shut-off valve 150 for example, shut-off valve 550 may remain in a closed position due to a negative pressure within the mask until the wearer exhales or the pressure within breathable air zone 522 is no longer greater than the force of the resilient member.

In an exemplary embodiment, actuator 551 in the form of an elastomeric button acts as a resilient member that biases actuator 551 towards an open position. Actuator 551 may include a flexible web 556 attached to an outer wall 523 of mask body 520 to support actuator 551 and/or bias shut-off valve 550 to an open position. Flexible web 556 is formed of a flexible or compliant material that is able to elastically deform when actuator 551 is pressed inwardly by a wearer, as shown in FIG. 5*c*, for example. In a closed position, flexible web 556 is flexed and/or deformed causing sealing pads 552*a*, 552*b* to pivot by contacting actuation tabs 547*a*, 547*b*, for example. Flexure and/or deformation of elastomeric web is desirably limited to the elastic regime such that elastomeric web is able to repeatedly return to an original configuration in which the shut-off valve is in an open position.

In an exemplary embodiment, actuator 551 is attached to mask body 520 such that a seal is formed between actuator 551 and mask body 520. For example, a portion of actuator 551 may be joined to mask body 520 to provide an adequate seal, for example by over-molding. Other suitable seal may be provided using gaskets, flanges, adhesive, interference fits, molding techniques, sonic welding, and other suitable techniques as known in the art. A sufficient seal proximate actuator 551 prevents ingress of unfiltered air from the external environment when shut-off valve 550 is in an open, closed, or intermediate position.

Other resilient members may be provided in place of or in addition to a flexible web of actuator 551. In some exemplary embodiments, actuator 551 is not attached to sealing pads 552*a*, 552*b*. A resilient member such as flexible web 556 biases actuator 551 to an open position and one or more additional members, such as spring members 558*a*, 558*b* bias sealing pads 552*a*, 552*b* to an open position. Spring members 558*a*, 558*b* may comprise any suitable spring to bias sealing pads 552*a*, 552*b* to an open position including a coil spring, leaf spring, elastomeric band or suitable resilient member as known in the art. In some exemplary embodiments, actuator 551 is attached to sealing pads 552*a*, 552*b* and a resilient member such as a flexible web and/or one or more spring members 558*a*, 558*b* bias both actuator 551 and sealing pads 552*a*, 552*b* towards an open position.

A respiratory mask according to the present disclosure provides several advantages. A shut-off valve operable between a closed position and an open position allows a wearer to easily perform a negative pressure fit test. A shut-off valve that closes inlet ports, for example, is believed to provide a more effective and reproducible fit check to verify the presence of an appropriate seal between a periphery of the mask and a user's face as compared to prior positive pressure fit devices. A respiratory mask according to the present disclosure thus may provide a solution to closing inlet valves that were inaccessible and not easily closed in many prior devices, for example. Respiratory masks as described above allow a negative pressure fit test to be performed by closing a single valve even if the mask may include more than one breathing air source components or more inlet ports, and does not require a wearer to engage multiple actuators or perform individual tests for each inlet port or breathing air source components, for example. A shut-off valve as described herein may be suitable for half-face respirators, full-face respirators, powered or positive pressure respirators, and other suitable respiratory protection devices.

The foregoing detailed description and examples have been given for clarity of understanding only. No unnecessary limitations are to be understood there from. It will be apparent to those skilled in the art that many changes can be made in the embodiments described without departing from the scope of the disclosure. Any feature or characteristic described with respect to any of the above embodiments can be incorporated individually or in combination with any other feature or characteristic, and are presented in the above order and combinations for clarity only. Thus, the scope of the present disclosure should not be limited to the exact details and structures described herein, but rather by the structures described by the language of the claims, and the equivalents of those structures.

What is claimed is:

1. A respiratory mask, comprising:
    a mask body defining a breathable air zone for a wearer and having two or more inlet ports configured to receive two or more breathing air source components; and
    a shut-off valve operable between a closed position and an open position the shut-off valve comprising an actuator being engageable by the wearer to move the shut-off valve into the closed position;
    wherein, in the closed position, the shut-off valve is configured to prevent fluid communication between the two or more inlet ports and the breathable air zone, and wherein the shut-off valve in the closed position is configured to achieve a negative pressure within the breathable air zone upon inhalation by the wearer to provide an indication of an adequate seal without leaks around a periphery of the mask body.

2. The respiratory mask of claim 1, wherein the indication is greater difficulty inhaling.

3. The respiratory mask of claim 1, wherein the mask body further comprises a compliant face contacting portion and the indication is an inward deflection of the compliant face contacting portion.

4. The respiratory mask of claim 1, wherein the shut-off valve is in the closed position when the actuator is depressed.

5. The respiratory mask of claim 4, wherein the actuator comprises a button including a flexible web.

6. The respirator mask of claim 5, wherein the flexible web biases the actuator to an open position corresponding to the shut-off valve in the open position.

7. The respirator mask of claim 5, wherein the flexible web is attached to the mask body to seal the actuator and the mask body.

8. The respiratory mask of claim 1, wherein the actuator that moves linearly between an open position and a closed position corresponding to the shut-off valve moving between the open position and the closed position.

9. The respiratory mask of claim 1, wherein the actuator that rotates between an open position and a closed position corresponding to the shut-off valve moving between the open position and the closed position.

10. The respiratory mask of claim 1, wherein the shut-off valve returns to the open position without further input to the actuator of the shut-off valve when the pressure in the breathable air zone is increased.

11. The respiratory mask of claim 1, wherein the shut-off valve returns to the open position without further input to the actuator of the shut-off valve when the wearer exhales.

12. The respiratory mask of claim 1, further comprising first and second filter cartridges attached to the mask body at two of the inlet ports.

13. The respiratory mask of claim 1, wherein the inlet ports are in fluid communication with a single fluid intake communication component comprising an inhalation port to allow fluid communication between the inlet ports and the breathable air zone.

14. The respiratory mask of claim 13, wherein the shut-off valve further comprises a sealing pad that contacts a sealing surface surrounding the inhalation port to prevent fluid communication between the breathing air source components and the inhalation port.

15. The respiratory mask of claim 14, wherein the sealing pad and actuator are integrally formed.

16. The respiratory mask of claim 14, wherein the sealing pad moves linearly between an open position and a closed position corresponding to the shut-off valve moving between the open position and the closed position.

17. The respiratory mask of claim 14, wherein the sealing pad pivots between an open position and a closed position corresponding to the shut-off valve moving between the open position and the closed position.

18. The respiratory mask of claim 14, wherein the fluid intake communication component comprises a first sealing surface and the shut-off valve comprises the sealing pad that contacts the first sealing surface when the shut-off valve is in the closed positi on.

19. The respirator mask of claim 13, wherein the fluid intake communication component further comprises a diaphragm and a second sealing surface, and the diaphragm contacts the second sealing surface to close the inhalation port in the absence of negative pressure within the breathable air zone.

20. The respiratory mask of claim 1, wherein the mask body further comprises a first chamber in fluid communication with each of the two or more inlet ports and a second chamber defining the breathable air zone, and a fluid intake communication component that allows fluid communication between the first chamber and the breathable air zone.

21. The respiratory mask of claim 1, wherein a first inlet port of the two or more inlet ports is in fluid communication with a first fluid intake communication component and a second inlet port of the two or more inlet ports is in fluid communication with a second fluid intake communication component.

22. The respiratory mask of claim 21, wherein the first fluid intake communication component comprises a first inhalation port and the second fluid intake communication component comprises a second inhalation port and the shut-off valve comprises first and second sealing pads, and wherein when the actuator is in the closed position the first and second sealing pads block the first and second inhalation ports to prevent fluid communication between the two or more breathing air sources and the breathable air zone.

23. The respiratory mask of claim 22, wherein the first and second sealing pads pivot between an open position and a closed position corresponding to the shut-off valve moving between the open position and the closed position.

24. The respirator mask of claim 22, wherein the first and second sealing pads move linearly between an open position and a closed position corresponding to the shut-off valve moving between the open position and the closed position.

25. The respirator mask of claim 1, wherein the shut-off valve comprises a biasing member biasing the shut-off valve to the open position from the closed position in the absence of an applied force by the wearer.

26. The respirator mask of claim 1, wherein the shut-off valve returns to the open position upon further input by the wearer.

27. A respiratory mask, comprising:
a mask body defining a breathable air zone for a wearer and having one or more inlet ports configured to receive one or more breathing air source components; and
a shut-off valve operable between a closed position and an open position, the shut-off valve comprising an actuator and a biasing member, the actuator being attached to the mask body such that a seal is formed between the actuator and the mask body in both open and closed positions and being engageable by the wearer to move the shut-off valve into the closed position, the biasing member biasing the shut-off valve to the open position from the closed position in the absence of an applied force by the wearer;
wherein, in the closed position, the shut-off valve is configured to prevent fluid communication between the one or more inlet ports and the breathable air zone, wherein the shut-off valve in the closed position is configured to achieve a negative pressure within the breathable air zone upon inhalation by the wearer.

28. The respiratory mask of claim 27, wherein the mask body comprises two or more inlet ports configured to receive two or more breathing air source components, and wherein, in the closed position, the shut-off valve is configured to prevent fluid communication between the two or more breathing air source components and the breathable air zone.

29. The respiratory mask of claim 27, wherein the shut-off valve in the closed position is configured to provide indication of the presence of leaks around a periphery of the mask body upon inhalation by the wearer.

30. The respirator mask of claim 27, wherein the biasing member comprises a resilient member to bias the shut-off valve to the open position.

31. The respiratory mask of claim 27, wherein when the mask body is positioned for use on the wearer and the negative pressure is achieved by closing the shut-off valve and inhaling, the shut-off valve remains in the closed position due to a negative pressure in the breathable air zone.

32. A respiratory mask, comprising:
a mask body defining a breathable air zone for a wearer and having one or more inlet ports configured to receive one or more breathing air source components; and
a shut-off valve operable between a closed position and an open position, the shut-off valve comprising an actuator being engageable by the wearer to move the shut-off valve into the closed position;
wherein, in the closed position, the shut-off valve is configured to prevent fluid communication between the one or more inlet ports and the breathable air zone, and wherein, when the mask body is positioned for use on the wearer, the shut-off valve in the closed position is configured to achieve a negative pressure upon inhalation by the wearer, and wherein the shut-off valve is configured to remain in the closed position due to the negative pressure in the breathable air zone.

33. The respiratory mask of claim 32, wherein the shut-off valve returns to the open position without further input to the actuator of the shut-off valve when the pressure in the breathable air zone is increased.

34. The respiratory mask of claim 32, wherein the shut-off valve returns to the open position without further input to the actuator of the shut-off valve when the wearer exhales.

* * * * *

UNITED STATES PATENT AND TRADEMARK OFFICE
CERTIFICATE OF CORRECTION

PATENT NO. : 9,950,202 B2
APPLICATION NO. : 13/757373
DATED : April 24, 2018
INVENTOR(S) : William Mittelstadt et al.

Page 1 of 1

It is certified that error appears in the above-identified patent and that said Letters Patent is hereby corrected as shown below:

In the Claims

<u>Column 17</u>
Line 6, in Claim 6, delete "respirator" and insert -- respiratory --, therefor.
Line 9 (approx.), in Claim 7, delete "respirator" and insert -- respiratory --, therefor.
Line 55, in Claim 18, delete "positi on." and insert -- position. --, therefor.
Line 56, in Claim 19, delete "respirator" and insert -- respiratory --, therefor.

<u>Column 18</u>
Line 20, in Claim 24, delete "respirator" and insert -- respiratory --, therefor.
Line 24, in Claim 25, delete "respirator" and insert -- respiratory --, therefor.
Line 28, in Claim 26, delete "respirator" and insert -- respiratory --, therefor.
Line 62, in Claim 30, delete "respirator" and insert -- respiratory --, therefor.

Signed and Sealed this
Sixth Day of November, 2018

Andrei Iancu
*Director of the United States Patent and Trademark Office*